United States Patent

Holberg et al.

[11] 4,225,254
[45] Sep. 30, 1980

[54] SURGICAL SCRUB SYSTEM

[76] Inventors: Steven E. Holberg, 411 NW. 88 Ave., Pembroke Pines, Fla. 33024; Ronald J. Sollitto, 222 Christie St., Ridgefield Park, N.J. 07660

[21] Appl. No.: 778,671

[22] Filed: Mar. 17, 1977

[51] Int. Cl.² ............... A46B 11/00; A61M 35/00
[52] U.S. Cl. .................... 401/119; 128/269; 141/18; 141/248; 141/351; 401/6; 401/11; 401/45; 401/192; 401/196; 401/206
[58] Field of Search .............. 401/6, 9, 118, 123, 401/129, 130, 44, 45, 196, 183, 205, 206, 261, 263, 184, 186, 289, 112, 119, 207, 278, 192, 279; 128/239, 65, 260, 67, 261, 274, 269, 251; 15/244 R, 145; 141/20.5, 104, 18, 335, 351, 248

[56] References Cited

U.S. PATENT DOCUMENTS

| | | | |
|---|---|---|---|
| 485,698 | 11/1892 | Ketchum | 128/274 X |
| 1,004,053 | 9/1911 | Madgett | 141/248 |
| 1,165,675 | 12/1915 | Ide | 141/335 |
| 1,355,026 | 10/1920 | Austin | 401/278 X |
| 1,454,208 | 5/1923 | Brackett | 141/335 |
| 1,470,903 | 10/1923 | Ahlering | 401/279 |
| 1,616,551 | 2/1927 | Rosenberg | 401/119 |
| 1,935,639 | 11/1933 | Keeshan | 401/192 |
| 1,973,158 | 9/1934 | Small et al. | 401/278 X |
| 2,280,398 | 4/1942 | Harvey | 401/119 |
| 2,438,338 | 3/1948 | Horn | 401/205 |
| 2,810,150 | 10/1957 | Ellman | 15/244 R |
| 2,845,964 | 8/1958 | Harland | 141/104 |
| 2,860,359 | 11/1958 | James | 401/183 |
| 3,070,823 | 1/1963 | Heinig | 401/6 |
| 3,103,682 | 9/1963 | Markle | 128/269 X |
| 3,294,126 | 12/1966 | Barton | 141/104 X |
| 3,508,547 | 4/1970 | Deuschle | 128/269 |
| 3,731,682 | 5/1973 | Fielding | 128/269 X |
| 3,818,911 | 6/1974 | Fournier | 128/269 |
| 3,847,151 | 11/1974 | D'Alessandro et al. | 128/269 |
| 3,871,425 | 3/1975 | Fee et al. | 141/351 X |
| 4,004,854 | 1/1977 | Breer | 401/205 |

FOREIGN PATENT DOCUMENTS

| | | | |
|---|---|---|---|
| 28633 | 3/1925 | France | 141/351 |
| 104680 | 8/1937 | United Kingdom | 141/351 |
| 748246 | 4/1956 | United Kingdom | 401/196 |

*Primary Examiner*—Edgar S. Burr
*Assistant Examiner*—Steven A. Bratlie
*Attorney, Agent, or Firm*—Samuelson & Jacob

[57] ABSTRACT

A surgical scrub system used in an operating room for dispensing any selected one of a plurality of sterile liquids and applying the selected liquid to an area of the body of a patient while maintaining the sterile condition desired at that area, the scrub system including a scrub device constructed primarily of sterilizable materials and a dispensing arrangement to which the scrub device may be aseptically coupled for transfer of the selected liquid to the scrub device.

18 Claims, 18 Drawing Figures

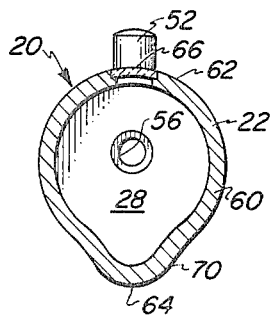
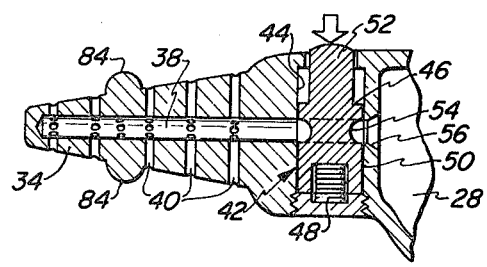
FIG. 4  FIG. 5
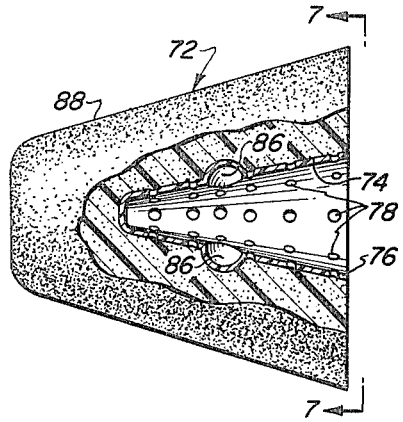
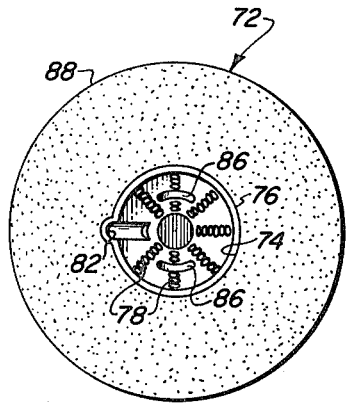
FIG. 6  FIG. 7
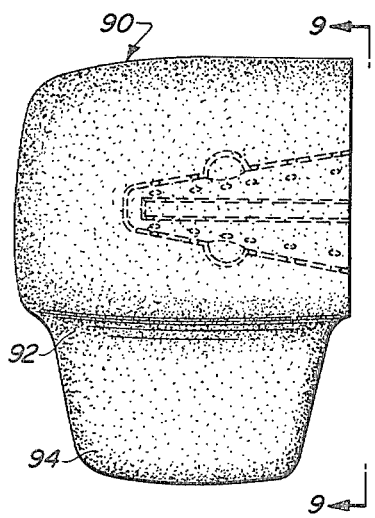
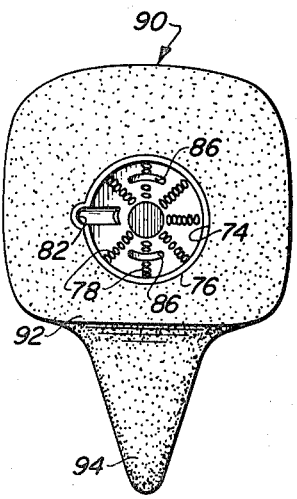
FIG. 8  FIG. 9

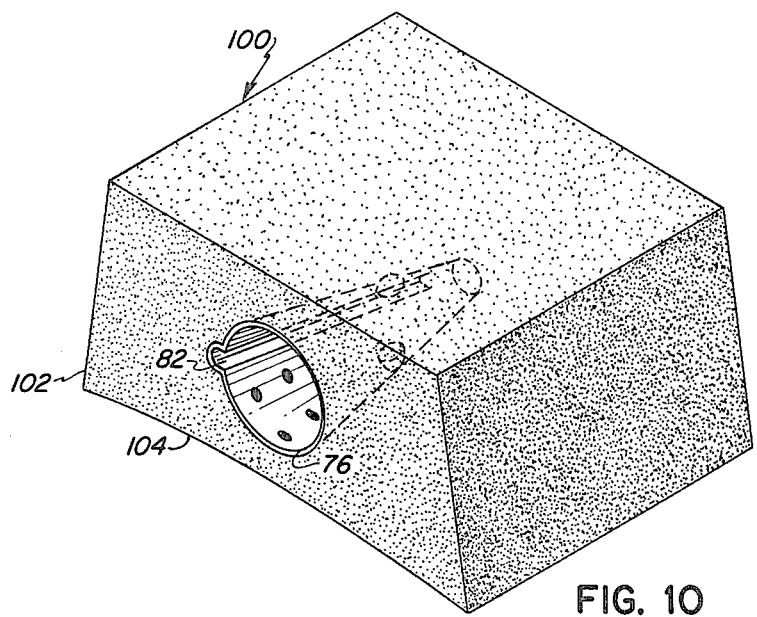
FIG. 10
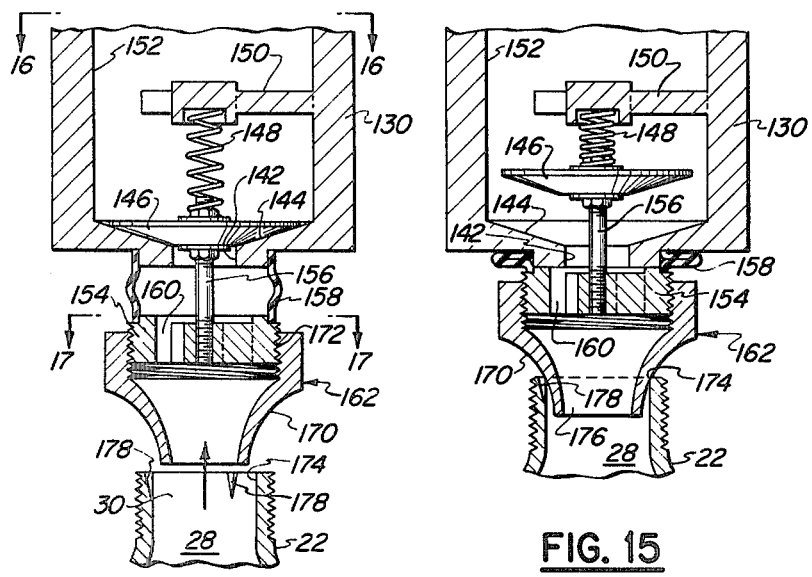
FIG. 14
FIG. 15
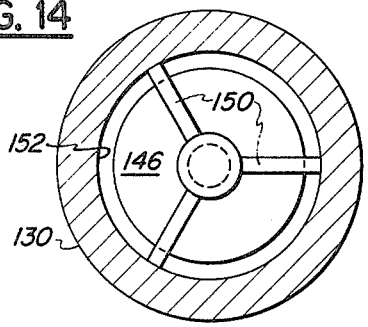
FIG. 16
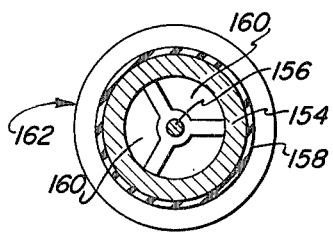
FIG. 17
FIG. 18

SURGICAL SCRUB SYSTEM

The present invention relates generally to the field of aseptic surgery and pertains, more specifically, to a surgical scrub system for use in an operating room.

Current surgical procedures require antiseptic cleansing of the area of a patient's body where the surgery is to be performed. Usually, the area is cleansed by applying one or more sterile liquids, such as antiseptic scrub, antiseptic solution, or sterile water to the area, the procedure being carried out within the operating room. In many operating rooms, the liquids are applied by pouring a selected liquid into a pan, immersing a swab into the liquid in the pan and then scrubbing the appropriate area of the body of the patient. Often, the swab is merely a sponge held within the grip of a pair of forceps. At best, the procedure is messy, due to the open pan the the constant back and forth travel of the sponge between the pan and the patient. In addition, the procedure is wasteful of time and effort, as well as of excess liquid which becomes scattered or discarded.

In an effort to overcome the drawbacks outlined above, dispensing devices have been developed in which an antiseptic liquid is contained within the device itself, which is in the form of a hollow handle, and is dispensed to a sponge attached to the device, the entire sponge and handle assembly serving as a cleansing unit. In later developments, the unit has been made disposable so that once the self-contained liquid is exhausted, the unit is discarded. Such devices, while convenient, become expensive in that they can be used only once. It may be necessary to use several disposable units in a single procedure, especially where several different liquids are required. In addition, the discarded units add to an already burgeoning disposal problem.

It is an object of the present invention to provide a scrub system for use in an operating room for dispensing any selected one of a plurality of sterile liquids and applying the selected liquid to an area of the body of a patient under aseptic conditions, the system thus making available immediately any one of the plurality of sterile liquids in any needed quantity with a minimum of waste and with increased ease.

Another object of the invention is to provide a system of the type described and in which aseptic conditions are maintained through the use of sterilizable materials in critical components of the system.

Still another object of the invention is to provide a surgical scrub device constructed of sterile and sterilizable materials and capable of being coupled aseptically to a dispenser in the operating room, the dispenser being capable of operation to dispense a selected one of several sterile liquids to the coupled scrub device with a minimum of waste and with relative ease.

A further object of the invention is to provide a surgical scrub device of the type in which a sterile liquid is fed from a hollow handle to a scrubbing swab, the scrubbing swab being selectively attached and detached for ease of use and disposal.

A still further object of the invention is to provide a surgical scrub device of the type described and in which the device has a handle configuration which facilitates proper use of the device and in which swabs of different surface contour configurations are interchangeably attached to the handle, with each surface contour configuration appropriately oriented relative to the handle.

Another object of the invention is to provide a system and device of the type described, and which is rugged and will withstand rigorous repeated use over a long useful life under operating room conditions.

The above objects, as well as still further objects and advantages, are attained by the present invention, which may be described briefly as a surgical scrub system at least a portion of which is to be placed in an essentially permanent installation in an operating room for dispensing any selected one of a plurality of sterile liquids and applying the selected liquid to an area of the body of a patient while maintaining the sterile condition desired at said area, the scrub system comprising a plurality of supply reservoirs associated with the essentially permanent installation, one supply reservoir for each sterile liquid to be dispensed, a dispensing head associated with the essentially permanent installation, selector means associated with the essentially permanent installation and communicating with each supply reservoir and with the dispensing head for selectively opening communication between the dispensing head and any one of the supply reservoirs, an operator coupled with the selector means and capable of manual actuation to any one of a plurality of selected positions, each position corresponding to the communication of the dispensing head with one of the supply reservoirs, for manually selecting which of the supply reservoirs will communicate with the dispensing head, a hollow handle constructed of a sterilizable material, such as stainless steel, the handle extending longitudinally between first and second ends and including a chamber therein, a dispensing tip constructed of a sterilizable material and located at the first end of the handle, the tip having an external surface, an internal cavity and passages between the cavity and the external surface, a valve constructed of sterilization material and located in the handle for selectively opening and closing communication between the cavity and the chamber, an opening located at the second end of the handle and communicating with the chamber, a coupling member constructed of a sterilizable material, such as stainless steel, removably securable to the dispensing head which, as a result of the association with the permanent installation, ordinarily is not sterile, the coupling member having an external configuration complementary to the opening in the handle such that the handle is capable of being coupled acceptically with the non-sterile dispensing head via the coupling member for placing the selected liquid in the chamber of the handle while maintaining the handle sterile, and a porous swab, the external surface of the dispensing tip including means for coupling the porous swab thereto for selective attachment and detachment such that a liquid in the chamber will be passed to the swab through the valve, the cavity and the passages for application to the area of the patient's body.

The invention will be more fully understood, while still further objects and advantages will become apparent, in the following detailed description of embodiments thereof illustrated in the accompanying drawing, in which:

FIG. 4 is a transverse cross-sectional view taken along line 4—4 of FIG. 3;

FIG. 5 is a fragmentary cross-sectional view of a portion of the scrub device of FIG. 2, but with component parts in another operating position;

FIG. 6 is an elevational view of a swab;

FIG. 7 is an end view of the swab, taken in the direction of arrows 7—7 in FIG. 6;

FIG. 8 is an elevational view of another swab;

FIG. 9 is an end view of the swab, taken in the direction of arrows 9—9 in FIG. 8;

Figure 11:
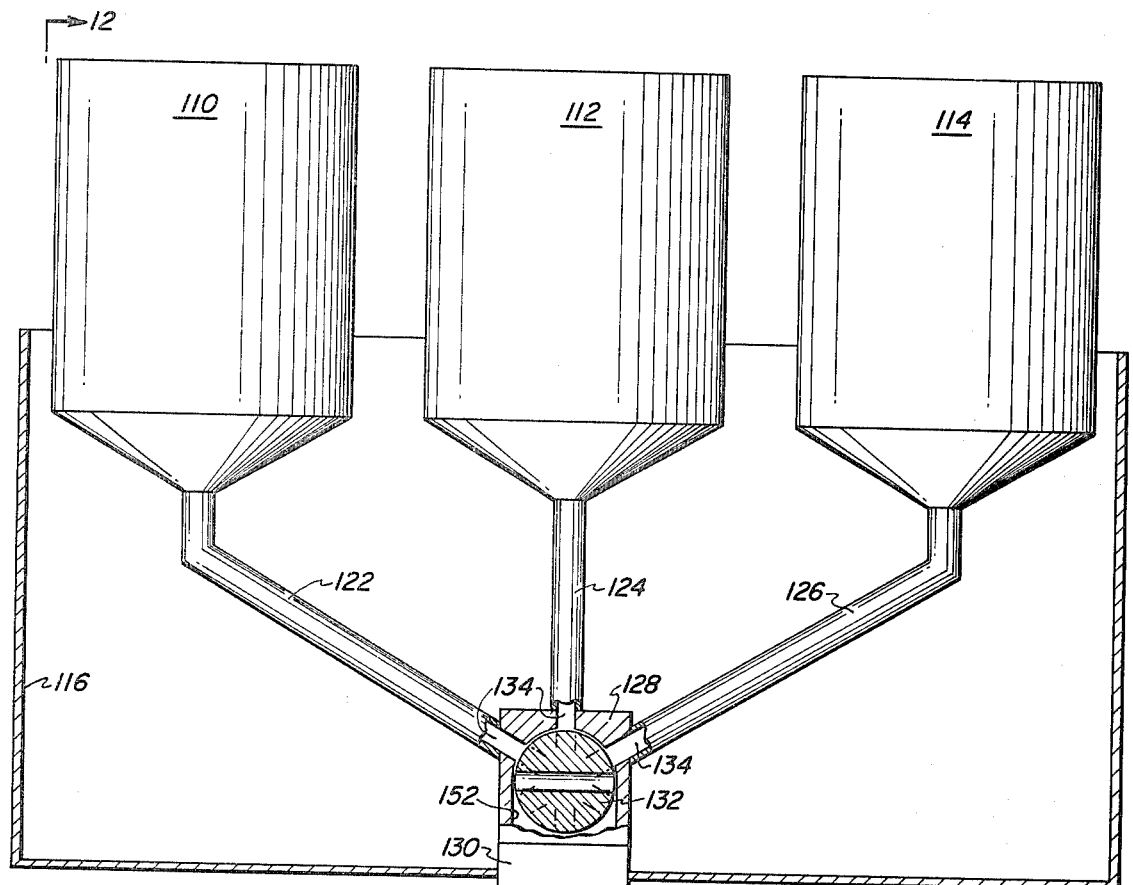
Figure 12:
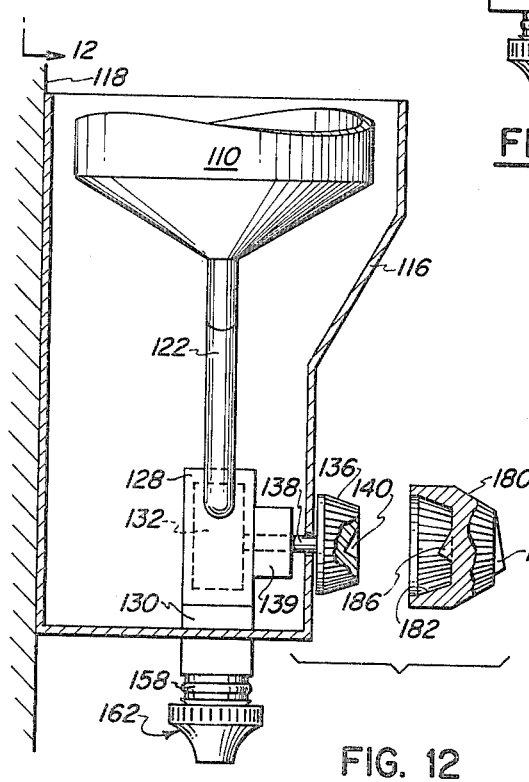
Figure 13:
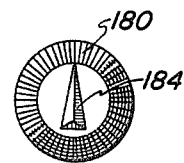

FIG. 10, which appears on the same sheet with FIGS. 14 through 18, is a perspective view of still another swab;

FIG. 11 is a front elevational view of a dispenser of the surgical scrub system constructed in accordance with the invention, portions of the dispenser being broken away to illustrate internal details;

FIG. 12 is a cross-sectional view taken along line 12—12 of FIG. 11;

FIG. 13 is an enlarged front elevational view of a component part shown in FIG. 12;

FIG. 14 is a fragmentary cross-sectional view of portions of the components of the system;

FIG. 15 is a fragmentary cross-sectional view similar to FIG. 14, but with the illustrated parts in another operating position;

FIG. 16 is a cross-sectional view taken along line 16—16 of FIG. 14;

FIG. 17 is a cross-sectional view taken along line 17—17 of FIG. 14; and

FIG. 18 is a partially sectioned elevational view of a coupling member employed in the system.

Figure 1:
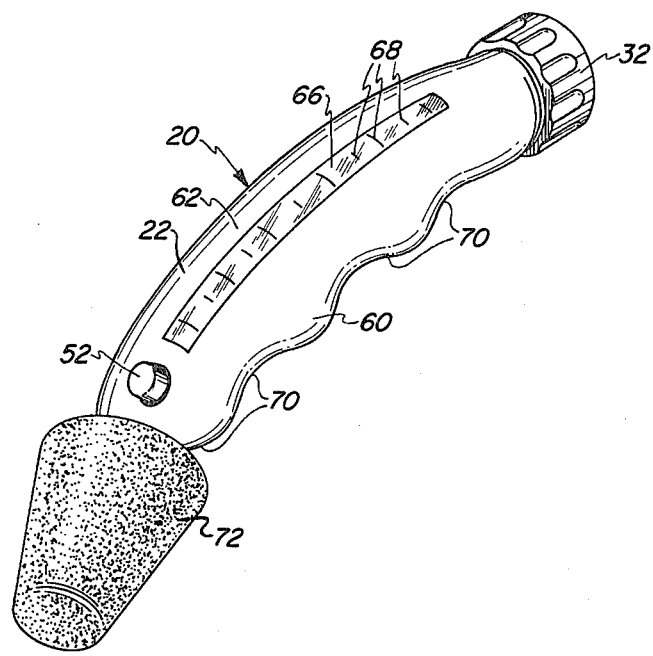
FIG. 1 is a perspective view of a surgical scrub device of a surgical scrub system constructed in accordance with the invention.
Figure 2:
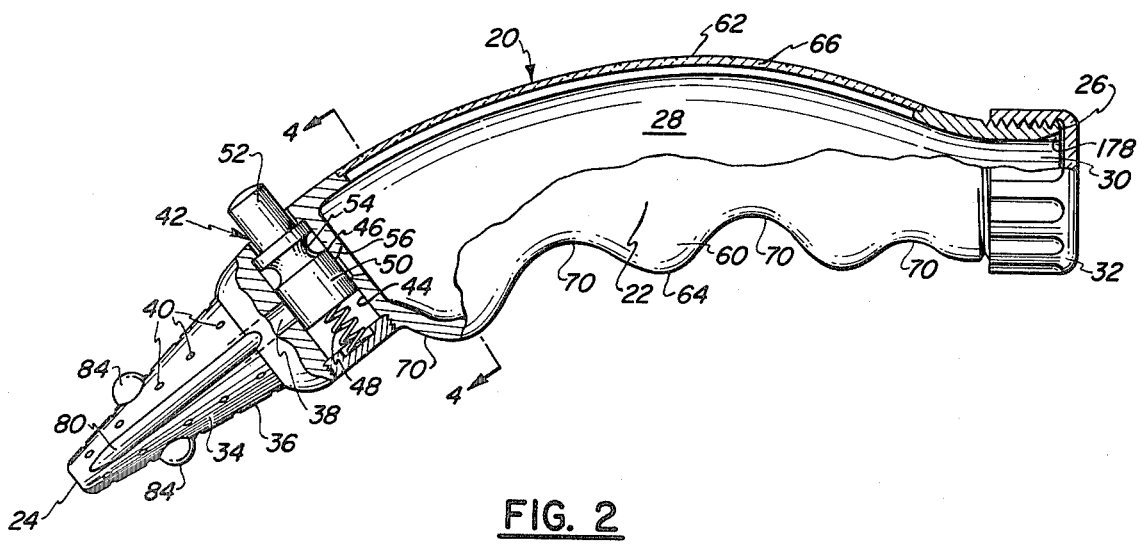
FIG. 2 is a side elevational view of the scrub device with the swab removed and portions broken away to reveal internal details.
Figure 3:
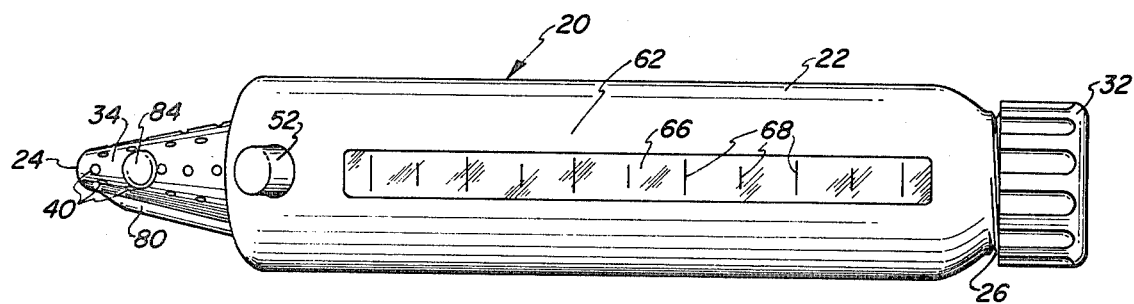
FIG. 3 is a top plan view of the scrub device of FIG. 2.

Referring now to the drawing, and especially to FIGS. 1 through 3 thereof, a surgical scrub device, which is a component of the surgical scrub system of the invention, is illustrated at 20. Scrub device 20 has a hollow handle 22 extending longitudinally between a first end 24 and a second end 26. A chamber 28 within the handle 22 has an opening 30 at end 26, and a screw cap 32 closes the opening 30.

Turning now to FIGS. 4 and 5, as well as FIGS. 1 through 3, a dispensing tip 34 is located at the other end 24 of the handle 22 and includes an external surface 36, an internal cavity 38 and a plurality of passages 40 running between the cavity 38 and the external surface 36. A valve 42 is placed between the chamber 28 and the cavity 38 and selectively opens and closes communication between the chamber and the cavity. Valve 42 has a cylindrical bore 44 within which a valve spool 46 is mounted for sliding movement between a first position shown in FIG. 2 and a second position shown in FIG. 5. A helical spring 48 biases the valve spool 46 upwardly into the first position where a skirt 50 closes communication between chamber 28 and cavity 38 and a button portion 52 of the valve spool 46 projects upwardly from the handle 22. Upon pressing downwardly upon button portion 52, as illustrated by the arrow in FIG. 5, the valve spool 46 is urged to the second position where an annular groove 54 in the valve spool 46 is aligned with an aperture 56 and cavity 38 to open communication between chamber 28 and cavity 38. In this manner, any liquid in chamber 28 is selectively passed to cavity 38 by pressing button portion 52.

Handle 22 includes a hand grip 60 extending between the ends 24 and 26. Hand grip 60 has an upperside 62 and an underside 64. Upperside 62 carries a transparent window 66 having graduations 68 thereon so that the amount of liquid in chamber 28 is indicated visibly. Hand grip 60 is arched, with upperside 62 being convex, and the underside 64 is provided with contoured finger grip portions 70. Thus, handle 22 is gripped readily and held with the dispensing tip 34 angled downwardly and the button portion 52 located for ready actuation by the thumb of the user.

A porous swab, illustrated in FIG. 1 in the form of a sponge 72, is affixed to the dispensing tip 34 so that liquid in the chamber 28 may be dispensed selectively to the sponge 72 by pressing button portion 52, thereby enabling the liquid to pass into the cavity 38, through passages 40 to the sponge 72. The sponge 72 is wiped over an area of the body of a patient to cleanse the area with the liquid. As best seen in FIGS. 6 and 7, sponge 72 has a socket 73 with a configuration generally complementary to the external surface 36 of dispensing tip 34. A ferrule 76 of resiliently flexible material, such as a semi-rigid synthetic resin material, lines the socket 74 and carries a plurality of openings 78 passing through the ferrule 76. In order to orient the ferrule 76, and the sponge 72, relative to the dispensing tip 34, orienting means are provided in the form of a longitudinal key 80 on the dispensing tip 34 and a complementary longitudinal keyway 82 in the ferrule 76. Engagement of key 80 within keyway 82 assures the appropriate orientation of sponge 72 relative to dispensing tip 34 and registration of openings 78 with passages 40. Openings 78 may be made larger in diameter than passages 40 in order to allow for slight misalignment.

Once in place, sponge 72 is retained upon the dispensing tip 34 by detachable coupling means shown in the form of detents including detent protrusions 84 on the dispensing tip 34 and complementary detent recesses 86 in ferrule 76. The tapered configuration of the dispensing tip 34, together with the flexible nature of the ferrule 76 and the resilient properties of the sponge 72 enables the sponge 72 to be pushed onto the dispensing tip 34 and the ferrule 76 to flex until detent protrusions 84 are seated within complementary detent recesses 86 and the sponge 72 is secured on the handle 22. Sponge 72 is selectively removed for replacement by pulling upon the sponge to reverse the assembly process and disengage the detent protrusions 84 from detent recesses 86, thereby detaching the sponge 72 from handle 22.

Sponge 72 is a general purpose sponge and has an external surface 88 with a frusto-conical surface contour. Hence, the orientation of the external surface 88 relative to handle 22 is of little moment. However, where the swab is to be provided with a special shape for a special purpose, orientation is important. Thus, where the swab is in the form of sponge 90, as illustrated in FIGS. 8 and 9, the external surface 92 is provided with a contour configuration which includes an elongate rib 94 extending in a generally longitudinal direction. Sponge 90 is an interdigital sponge to be used for applying liquid to the areas surrounding the patient's digits. The keyway 82 of ferrule 76 in sponge 90 is located relative to rib 94 so that when sponge 90 is affixed to dispensing tip 34 rib 94 will project downwardly, i.e., in the direction from the upperside 62 toward the underside 64 of the hand grip 60. In this manner, the special contour configuration of sponge 90 is coupled with the configuration of the handle 22 for optimum usage.

Another alternate sponge 100, illustrated in FIG. 10, is provided for scrubbing abdominal areas of the patient's body. Sponge 100 has an external surface 102 with a contour configuration which includes a concave, generally cylindrical surface portion 104 oriented relative to keyway 82 in ferrule 76 so as to face downwardly, i.e., in the same direction as the underside 64 of hand grip 60. Thus, sponge 100 may be secured to handle 22 with the special contour configuration appropriately oriented relative to the hand grip 60.

Referring now to FIGS. 11 through 18, the surgical scrub system is to be used in an operating room and any selected one of a plurality of sterile liquids is to be supplied to surgical scrub device 20 for applying the selected liquid to an area of the body of a patient in the operating room. As best seen in FIGS. 11 and 12, the system includes a plurality of supply reservoirs, here shown in the form of tanks 110, 112 and 114, supported within a housing 116 mounted upon a wall 118 of the operating room. Each tank contains a particular sterile liquid used in the scrubbing procedure. For example, tank 110 may contain an antiseptic solution, tank 112 may contain sterile water and tank 114 may contain an antiseptic scrub. Each tank 110, 112 and 114 is connected to a corresponding conduit 122, 124 and 126, and all of the conduits lead to a manifold 128 located below the tanks so that liquid will be fed by gravity from the tanks to manifold 128. Also connected to the manifold 128 is a dispensing head 130 which lies beneath the manifold. Selector means in the form of a rotary valve 132 is placed between the manifold inlets 134 and the dispensing head 130. In the position illustrated in FIG. 11, all of the inlets 134 are closed by the rotary valve 132. However, by rotating the rotary valve 132, any one of the inlets 134 can be opened to open communication between a corresponding conduit 122, 124 or 126 and the dispensing head 130. Rotation of the rotary valve 132 among the various positions is accomplished by an operator in the form of knob 136 carried by shaft 138 which is connected to rotary valve 132. Thus, any one of the tanks 110, 112, or 114 may be selectively placed in communication with the dispensing head by manual indexing of knob 136. A return mechanism 139 is coupled to shaft 138 and returns rotary valve 132 and knob 136 to the "off" position illustrated in FIG. 11 upon release of knob 136. Thus, rotary valve 132 is normally biased into the "off" position by return mechanism 139. A recessed pointer 140 on knob 136 indicates visually the position of the rotary valve 132.

Turning to FIGS. 14 through 17, dispensing head 130 includes an orifice 142 surrounded by a valve seat 144. A valve member 146 is biased against the valve seat 144 by a helical spring 148 which extends between the valve member 146 and a spider 150 affixed within the throat 152 of the dispensing head 130. An actuator in the form of a perforated disk 154 is carried by a rod 156 secured to the valve member 146. A sleeve 158 of a flexible, non-porous material, such as rubber, extends between the disk 154 and the valve seat 144 to enclose the orifice 142 and the perforations 160 in the disk 154. Disk 154 is movable upwardly and downwardly between the lower location illustration in FIG. 14, wherein orifice 142 is sealed by valve member 146, and no liquid is dispensed through dispensing head 130, and the upper location illustrated in FIG. 15, wherein the orifice 142 is open so that liquid can be dispensed through dispensing head 130.

Handle 22 is constructed of sterilizable materials and may be used over and over again by merely sterilizing the handle before each use. Thus, the hand grip 60, the dispensing tip 34 and screw cap 32 preferably are constructed of stainless steel. Valve 42 is constructed so that all of the component parts of the valve can be fabricated of a sterilizable material such as stainless steel. The window 66 is also fabricated of a sterilizable material such as glass. The entire handle 22 is free of any seams, sharp corners and crevices which could collect septic matter. It is pointed out that the majority of hospitals and operating rooms sterilize utensils by heat; hence, the materials chosen for the component parts of handle 22 must be able to withstand the heat employed for sterilization. The illustrated construction attains that goal while providing a rugged, utilitarian utensil.

A selected liquid is dispensed from the dispensing head 130 into the chamber 28 within the handle 22 of the scrub device 20 by indexing the rotary valve 132 to the appropriate position, coupling the opening 30 of handle 22 with the disk 154 and moving the disk from the location shown in FIG. 14 toward the location shown in FIG. 15. In order to maintain the sterile conditions essential to the surgical procedure, the handle 22 must be sterile. Since the dispensing head 130 is a part of a permanent installation in the operating room, it will not be sterile; hence, the handle 22 must be aseptically coupled to the dispensing head 130. In addition, selection of the sterile liquid is to be done by the same user who is holding the handle 22 and, since the knob 136 is a part of the same permanent installation, the knob will not be sterile and means must be provided for aseptic indexing of the knob 136.

Aseptic coupling of the handle 22 with the dispensing head 130 is attained through the use of a sterilizable coupling member shown in the form of nozzle 162, fabricated of a sterilizable material such as stainless steel. As best seen in FIG. 18, nozzle 162 has a collar 164 with an internal thread 166. A tapered portion 168 depends from collar 164 and provides a shoulder 170 along the outside surface thereof. Nozzle 162 is rendered sterile and is then coupled to the disk 154 by engaging the internal thread 166 with an external thread 172 on the disk 154. The opening 30 of chamber 28 in handle 22 is then moved upwardly toward nozzle 162, as seen in FIG. 14, until tapered portion 168 enters opening 30 and the rim 174 of the opening 30 engages complementary shoulder 170 of the nozzle 162. Continued upward movement of handle 22 will move the nozzle 162 upwardly, thereby moving disk 154 toward the location shown in FIG. 15 and opening orifice 142. Depending upon the position of the rotary valve 132, a selected liquid will then flow from one of the tanks 110, 112 or 114, through the internal passage 176 within nozzle 162 and into the handle 22. Since the valve 42 in the handle is normally closed, the chamber 28 will be filled. Notches 178 may be placed in rim 174 to vent air from chamber 28 as the chamber is filled. The filling of chamber 28 may be observed through window 66 and can be stopped at any desired point.

In order to preclude contamination of the user's hand when operating rotary valve 132, a sterile shield 180 may be placed over knob 136, as seen in FIGS. 12 and 13. Shield 180 is coupled to knob 136 by complementary inner surface 182 and carries a pointer 184 which matches pointer 140 on knob 136 by virtue of the entrance of key 186 into recessed pointer 140. Shield 180 may be sterilizable or disposable.

Once the chamber 28 of handle 22 is filled with the selected liquid in the appropriate amount, the handle 22 is lowered from nozzle 162, disk 154 drops and the orifice 142 is closed. Opening 30 of handle 22 is then capped with screw cap 32 and an appropriate sterile porous swab is attached to dispensing tip 34. The cleansing procedure can then proceed, with the handle being refilled and the swabs being replaced as necessary.

Thus, the surgical scrub system of the invention provides a convenient and abundant source of a variety of sterile liquids ready for selection and use in any scrub procedure. A single surgical scrub device is provided with interchangeable scrub swabs in the form of sponges of various configurations for varied purposes, each sponge being attached or detached at will. The rugged handle is totally sterilizable, rendering it usable for an indefinite number of reuses. Liquids are transferred from the source to the handle under aseptic conditions and in just the right amounts, thereby eliminating waste and mess, while maintaining the appropriate sterile conditions for surgery.

It is to be understood that the above detailed description of embodiments of the invention is provided by way of example only. Various details of design and construction may be modified without departing from the true spirit and scope of the invention as set forth in the appended claims.

The embodiments of the invention in which an exclusive property or privilege is claimed are defined as follows:

1. A surgical scrub system at least a portion of which is to be placed in an essentially permanent installation in an operating room for dispensing any selected one of a plurality of sterile liquids and applying the selected liquid to an area of the body of a patient while maintaining the sterile condition desired at said area, said scrub system comprising:
    a plurality of supply reservoirs associated with said essentially permanent installation, one supply reservoir for each sterile liquid to be dispensed;
    a dispensing head associated with said essentially permanent installation;
    selector means associated with said essentially permanent installation and communicating with each supply reservoir and with the dispensing head for selectively opening communication between the dispensing head and any one of the supply reservoirs;
    an operator coupled with the selector means and capable of manual actuation to any one of a plurality of selected positions, each position corresponding to the communication of the dispensing head with one of the supply reservoirs, for manually selecting which of the supply reservoirs will communicate with the dispensing head;
    a hollow handle constructed of a sterilizable material, such as stainless steel, the handle extending longitudinally between first and second ends and including a chamber therein;
    a dispensing tip constructed of a sterilizable material and located at the first end of the handle, the tip having an external surface, an internal cavity and passages between the cavity and the external surface;
    a valve constructed of sterilizable material and located in the handle for selectively opening and closing communication between the cavity and the chamber;
    an opening located at the second end of the handle and communicating with the chamber;
    a coupling member constructed of a sterilizable material, such as stainless steel, and removably securable to the dispensing head which, as a result of said association with the permanent installation, ordinarily is not sterile, said coupling member having an external configuration complementary to the opening in the handle such that the handle is capable of being coupled aseptically with the non-sterile dispensing head via the coupling member for placing the selected liquid in the chamber of the handle while maintaining the handle sterile; and
    a porous swab;
    the external surface of the dispensing tip including means for coupling the porous swab thereto for selective attachment and detachment such that a liquid in the chamber will be passed to the swab through the valve, the cavity and the passages for application to said area.

2. The invention of claim 1 wherein
    the selector means includes means for closing communication between the dispensing head and all of the supply reservoirs; and
    the operator is movable to a further position wherein communication between the dispensing head and all of the supply reservoirs is closed.

3. The invention of claim 2 including means for normally biasing the operator into said further position.

4. The invention of claim 1 wherein:
    the dispensing head includes an actuator movable between a first location, wherein the selected liquid is dispensed from the dispensing head, and a second location, wherein dispensing of the selected liquid through the dispensing head is precluded; and
    the coupling member is removably securable to the actuator such that upon coupling the handle with the actuator the actuator may be moved between the first and second locations by the corresponding movement of the handle for dispensing the selected liquid to the handle.

5. The invention of claim 4 wherein:
    the dispensing head includes biasing means biasing the actuator toward the second location;
    the external configuration of the coupling member includes a shoulder; and
    the handle includes a rim extending around the opening therein, the rim being engageable with the shoulder such that the actuator will be moved from the second location to the first location in response to the corresponding movement of the handle.

6. The invention of claim 5 wherein:
    the actuator is movable upwardly and downwardly, the first location being located above the second location;
    the biasing means biases the actuator downwardly into the second location;
    the actuator is movable upwardly into the first location in response to movement of the rim of the handle upwardly against the shoulder of the coupling member, against the downward biasing force of the biasing means.

7. The invention of claim 6 wherein:
    the coupling member is threaded onto the actuator and includes an internal passage extending through the coupling member; and the internal passage of the coupling member communicates with the selected reservoir, through the dispensing head, upon upward movement of the coupling member and the corresponding movement of the actuator to the first location thereof, in response to corresponding upward movement of the handle while against the shoulder of the coupling member.

8. The invention of claim 1 wherein
the handle includes a sterilizable hand grip extending longitudinally between the ends of the handle, the hand grip having an upperside and an opposite underside, the hand grip being arched, with the upperside being convex, such that the dispensing tip is angled downwardly.

9. The invention of claim 8 including a transparent window constructed of a sterilizable material and located in the upperside of the hand grip for providing a visible indication of the amount of liquid in the chamber of the handle.

10. The invention of claim 8 including contoured finger grip portions of sterilizable material in the underside of the hand grip.

11. The invention of claim 8 wherein:
the porous swab has an internal socket complementary to the external surface of the dispensing tip and an external surface contoured to facilitate application of the selected liquid to said area of the body of the patient; and
the internal socket and the external surface of the dispensing tip include complementary orienting means for orienting the contoured external surface of the swab in a fixed relationship relative to the hand grip of the handle.

12. The invention of claim 11 wherein the orienting means includes a key and a keyway, both extending in a generally longitudinal direction aligned with said longitudinally extending handle.

13. The invention of claim 11 wherein the contoured external surface includes a concave, generally cylindrical surface portion oriented so as to face in the same direction as the underside of the handle.

14. The invention of claim 11 wherein the contoured external surface includes an elongate rib extending generally longitudinally and projecting in a direction extending from the upperside toward the underside of the handle.

15. The invention of claim 11 wherein the internal socket includes a ferrule lining the socket, said ferrule having openings corresponding in location to the passages in the dispensing tip for enabling the passage of the selected liquid through the ferrule to the porous swab.

16. The invention of claim 15 wherein the means for detachably coupling the porous swab to the external surface of the dispensing tip includes complementary detent members in the ferrule and on the external surface of the dispensing tip, at least the detent member on the external surface of the dispensing tip being constructed of sterilizable material.

17. The invention of claim 16 wherein the dispensing tip is tapered and the ferrule is constructed of a resiliently flexible material.

18. The invention of claim 1 including a sterile shield removably affixed to the operator and being selectively replaceable for maintaining the desired sterile condition while enabling manual operation of the operator.

* * * * *